US00PP36180P2

(12) United States Plant Patent
Woolmore

(10) Patent No.: US PP36,180 P2
(45) Date of Patent: Oct. 1, 2024

(54) ***PHORMIUM* PLANT NAMED 'KFPHPM18'**

(50) Latin Name: ***Phormium tenax* x *cookianum***
Varietal Denomination: KFPHPM18

(71) Applicant: Malcolm Woolmore, Auckland (NZ)

(72) Inventor: Malcolm Woolmore, Auckland (NZ)

( * ) Notice: Subject to any disclaimer, the term of this patent is extended or adjusted under 35 U.S.C. 154(b) by 0 days.

(21) Appl. No.: 18/389,340

(22) Filed: Nov. 14, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Phormium* cultivar named 'KFPHPM18' is disclosed, characterized by bronze foliage with a distinctive bright pink margin and streaks. Mature plant size of approximately 35 cm tall and wide. Foliage is upright to slightly arching. Plants are suitable for gardens, container cultivation and landscaping. The new variety is a *Phormium*, typically produced as an outdoor ornamental plant.

2 Drawing Sheets

Figure 1:
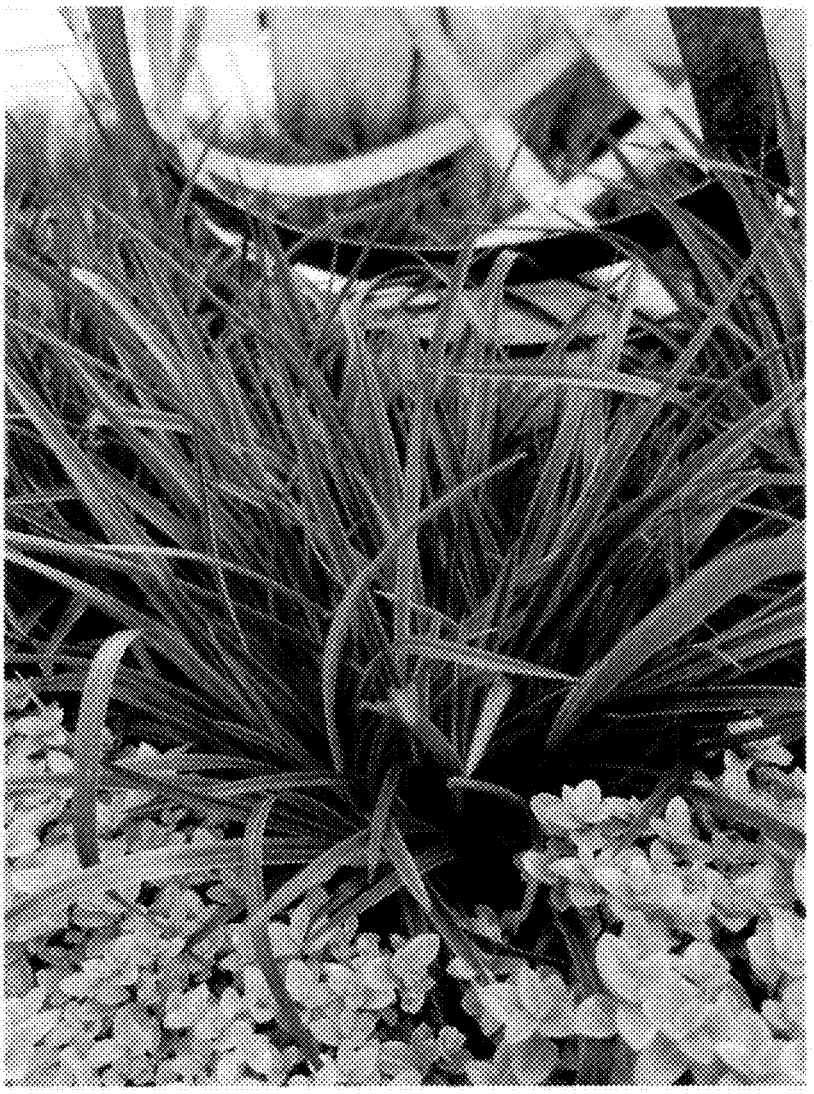

Latin name of the genus and species: *Phormium tenax* x *cookianum.*

Variety denomination: 'KFPHPM18'.

BACKGROUND OF THE INVENTION

The new cultivar is a product of chance discovery. The new variety was discovered as a naturally occurring whole plant mutation of the commercial variety *Phormium tenax* x *cookianum* 'PHOS2', U.S. Plant Pat. No. 20,249. The selection was made at a commercial nursery during 2015 in Whenuapai, New Zealand.

Asexual reproduction of the new cultivar 'KFPHPM18' was first performed at a commercial nursery in Whenuapai, New Zealand by vegetative divisions in 2015. Subsequent propagation by cutting and tissue culture has shown that the unique features of this cultivar are stable and reproduced true to type. Ten generations have been reproduced.

The following traits have been repeatedly observed and are determined to be the unique characteristics of 'KFPHPM18.' These characteristics in combination distinguish 'KFPHPM18' as a new and distinct *Phormium* cultivar:

1. Bronze foliage with a distinctive bright pink margin and streaks.
2. Mature plant size of approximately 35 cm tall and wide.
3. Upright to slightly arching foliage aspect.

PARENT COMPARISON

Plants of the new cultivar 'KFPHPM18' are similar to the parent in most horticultural characteristics. The new variety, however, differs in the following:

1. The new variety produces bronze foliage with distinctive bright pink margins and streaks; the parent variety has solid bronze foliage.
2. Mature plant size of the new variety is approximately 35 cm tall and wide; mature plant size of the parent variety is approximately 30 cm tall and wide 3. Foliage of the new variety is slightly wider than foliage of the parent variety.

COMMERCIAL COMPARISON

'KFPHPM18' can be compared to compared to the commercial variety *Phormium tenax* x *cookianum* 'PHOS4', unpatented. Plants of 'PHOS4' are similar to plants of 'KFPHPM18' in most horticultural characteristics, however, plants of 'KFPHPM18' differ in the following:

1. The new variety produces bronze foliage with distinctive bright pink margins and streaks; this comparator produces foliage which is bronze with lime green variegation.
2. Mature plant size of the new variety is approximately 35 cm tall and wide; mature plant size of this comparator is approximately 30 cm tall and wide
3. Foliage of the new variety is slightly wider than foliage of this comparator.

'KFPHPM18' can be compared to compared to the commercial variety *Phormium tenax* 'PKFJTB18', U.S. Plant Pat. No. 35,121. Plants of 'PKFJTB18' are similar to plants of 'KFPHPM18' in most horticultural characteristics, however, plants of 'KFPHPM18' differ in the following:

1. The new variety produces bronze foliage with distinctive bright pink margins and streaks; this comparator produces grey-brown foliage with dusky pink variegation and a very thin bright orange margin.
2. The new variety has glossy foliage; foliage of this comparator is matte.
3. Mature plant size of the new variety is approximately 35 cm tall and wide; mature plant size of this comparator is approximately 60 to 70 cm tall and 90 cm wide.
4. The new variety can be produced rapidly by division; this comparator is slow in production by division.

'KFPHPM18' can be compared to compared to the commercial variety *Phormium cookianum* 'Blondie', U.S. Plant Pat. No. 24,399. Plants of 'Blondie' are similar to plants of 'KFPHPM18' in most horticultural characteristics, however, plants of 'KFPHPM18' differ in the following:

1. The new variety produces bronze foliage with distinctive bright pink margins and streaks; this comparator produces creamy yellow foliage with green variegation and margins.
2. The new variety has upright to slightly arching foliage; foliage of this comparator is extremely arching.
3. Mature plant size of the new variety is approximately 35 cm tall and wide; mature plant size of this comparator is approximately 60 to 90 cm tall and 45 to 60 cm wide.

BRIEF DESCRIPTION OF THE PHOTOGRAPHS

The accompanying drawing in FIG. 1 illustrates in full color a typical plant of 'KFPHPM18' grown outdoors in Whenuapai, New Zealand. This plant is approximately 12 months old, in a 20 cm pot.

Figure 2:
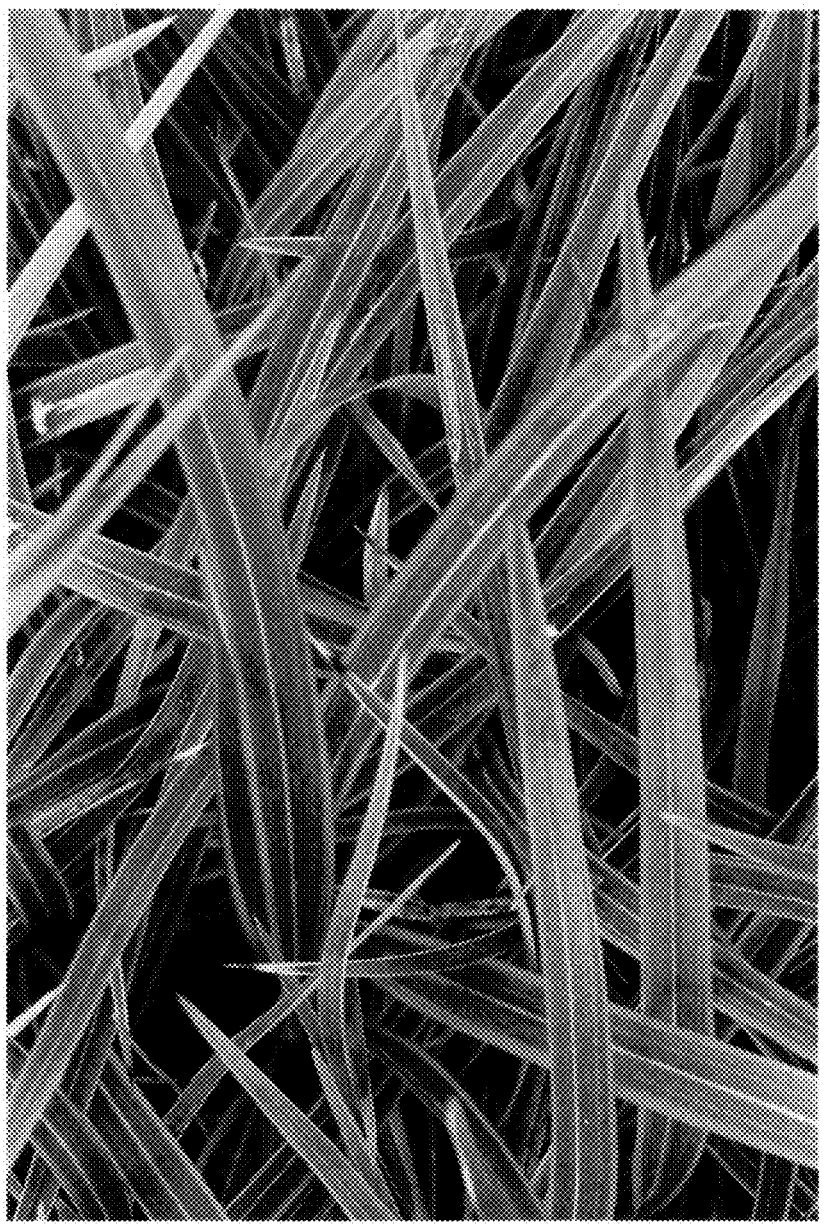

FIG. 2 illustrates a close-up view of typical foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KFPHPM18' plants grown outdoors in Dayton, OR. Temperatures ranged from about −2° C. to 8° C. at night to 5° C. to 28° C. during the day. No artificial light, photoperiodic treatments were given to the plants. Measurements and numerical values represent averages of typical plant types.

Botanical classification: *Phormium tenax* x *cookianum* KFPHPM18'.

PROPAGATION

Type of propagation typically used: Division.

PLANT

Growth habit: Upright, evergreen perennial.
Plant shape: Inverted triangle.
Height: Approximately 15 cm.
Plant spread: Approximately 28 cm.
Branching characteristics: Herbaceous shoots emerging basally.
Number of clumps per plant: Approximately 10 to 15 distinctive basal clumps, growing very densely together, in an approximately 8-month old plant.
Age of plant described: Approximately 8-months.

FOLIAGE

Leaf:

*Arrangement*.—Cauline.
*Compound or single*.—Single.
*Quantity of leaves per clump*.—15 to 25.
*Average length*.—Approximately 15 cm.
*Average width*.—Approximately 1.5 cm.
*Shape of blade*.—Linear.
*Aspect*.—Upright to slightly arching.
*Apex*.—Acuminate.
*Base*.—Cuneate.
*Margin*.—Entire.
*Texture of top surface*.—Glabrous, finely ridged.
*Texture of bottom surface*.—Glabrous, finely ridged.
*Texture*.—Upper surface glossy, lower surface slightly glossy. Entirely non-pubescent.
*Color*.—Young foliage upper side: Near R.H.S. Greyed-Purple N186B. Margin 186C flushed Red-Purple 72C. Young foliage under side: Near R.H.S. Greyed-Purple N186B. Margin 186C flushed Red-Purple 72C. Mature foliage upper side: Near R.H.S. Greyed-Purple N186B. Margin 186C flushed Red-Purple 72C. Streaks near 72C increasing with maturity in both size and intensity. Mature foliage under side: Near R.H.S. Greyed-Purple N186B. Margin 186C flushed Red-Purple 72C. Streaks near 72C increasing with maturity.
*Venation*.—Type: Parallel with 1 prominent, thin mid-vein. Width of mid vein: Approximately 1 mm. Venation coloration upper side: Near R.H.S. Greyed-Purple N186B, mid vein Greyed-Purple N187D. Venation coloration under side: Indistinguishable from leaf blade.

Petiole: Not present.

FLOWER

Not observed to date.

REPRODUCTIVE ORGANS

Not observed to date.

OTHER CHARACTERISTICS

Disease resistance: Neither resistance nor susceptibility to normal diseases and pests of *Phormium* have been observed.
Drought tolerance and cold tolerance: Tolerates temperatures just below 0° C. to 40° C. and can tolerate slight drought.
Fruit/seed production: Not observed.

What is claimed is:

1. A new and distinct cultivar of *Phormium* plant named 'KFPHPM18' as herein illustrated and described.

* * * * *